United States Patent
Ciancanelli (10) Patent No.: US 7,569,981 B1
(45) Date of Patent: Aug. 4, 2009

(54) ULTRAVIOLET GERMICIDAL LAMP BASE AND SOCKET

(75) Inventor: Gino Ciancanelli, Southbury, CT (US)

(73) Assignee: Light Sources, Inc., Orange, CT (US)

( * ) Notice: Subject to any disclaimer, the term of this patent is extended or adjusted under 35 U.S.C. 154(b) by 373 days.

(21) Appl. No.: 11/062,988

(22) Filed: Feb. 22, 2005

(51) Int. Cl.
    *H01J 5/48* (2006.01)
    *H01J 5/50* (2006.01)
    *H01R 13/52* (2006.01)

(52) U.S. Cl. ............... 313/300; 313/318.1; 439/677; 439/934; 439/617; 250/436

(58) Field of Classification Search ............... 313/318.01–318.03, 567, 621–623; 250/504 R; 422/121; 439/587, 336
    See application file for complete search history.

(56) References Cited

U.S. PATENT DOCUMENTS

| | | | |
|---|---|---|---|
| 2,227,739 A | 1/1941 | Pollard | |
| 2,836,646 A | 5/1958 | Paolinelli | |
| 3,601,699 A | 8/1971 | Norton, Jr. et al. | 324/158 F |
| 3,638,170 A | 1/1972 | Clement et al. | 339/135 |
| 4,623,823 A | 11/1986 | Engel | 315/58 |
| 4,700,101 A | 10/1987 | Ellner et al. | |
| 4,713,019 A * | 12/1987 | Gaynor | 439/232 |
| 4,906,891 A | 3/1990 | Takagi et al. | 313/318 |
| 4,949,007 A | 8/1990 | Takagi et al. | 313/318 |
| 4,985,002 A * | 1/1991 | Maisch et al. | 439/607 |
| 5,166,527 A | 11/1992 | Solymar | |
| 5,169,227 A | 12/1992 | Korte et al. | 362/226 |
| 5,239,226 A * | 8/1993 | Seredich et al. | 313/318.01 |
| 5,422,487 A | 6/1995 | Sauska et al. | |
| 5,701,050 A * | 12/1997 | Wolf et al. | 313/25 |
| 5,752,842 A | 5/1998 | Friederichs et al. | |
| 5,902,552 A | 5/1999 | Brickley | 422/121 |
| 5,968,455 A | 10/1999 | Brickley | 422/121 |

(Continued)

FOREIGN PATENT DOCUMENTS

| | | |
|---|---|---|
| WO | 01/30399 | 5/2001 |

(Continued)

OTHER PUBLICATIONS

International Search Report, Application No. PCT/US06/06087, Date Mailed Feb. 27, 2008.

(Continued)

*Primary Examiner*—Sikha Roy
*Assistant Examiner*—Tracie Green
(74) *Attorney, Agent, or Firm*—Cantor Colburn LLP (57) ABSTRACT

An ultraviolet gas discharge lamp having contact pins extending downward from a base cap toward an opposing end. The lamp is placed within a conduit or duct for disinfecting air or water flowing within the conduit. The reverse contact pins that extend toward the opposing end mate with contact holes in a socket attached to the conduit through which the lamp is inserted. The lamp is only energized when the lamp is fully inserted into the duct and is de-energized upon removing the lamp from the duct. A shield protects the pins. A window may be place in the base cap so as to visually confirm that the lamp is energized and radiating. A key and mating receiver may be used on the base cap and the socket so as to prevent accidental insertion of an inappropriate lamp.

21 Claims, 5 Drawing Sheets

U.S. PATENT DOCUMENTS

| | | | |
|---|---|---|---|
| 6,190,191 B1 | 2/2001 | Pasternak | 439/236 |
| 6,268,607 B1* | 7/2001 | Marsh et al. | 250/455.11 |
| 6,340,310 B2 | 1/2002 | Henrici et al. | |
| 6,500,387 B1 | 12/2002 | Bigelow | |
| 6,634,902 B1 | 10/2003 | Pirovic | |
| 6,641,419 B1* | 11/2003 | Richardson | 439/230 |
| 6,729,910 B2 | 5/2004 | Fuller | |
| 6,746,134 B1 | 6/2004 | Guzorek | 362/226 |
| 6,797,966 B2 | 9/2004 | Summers et al. | 250/492.1 |
| 6,809,326 B2 | 10/2004 | Disabito et al. | 250/504 |
| 6,838,057 B2 | 1/2005 | Russel et al. | 422/121 |
| 6,884,103 B1 | 4/2005 | Kovacs | |
| 7,025,616 B2* | 4/2006 | Hopper | 439/318 |
| 7,137,728 B2 | 11/2006 | Witham et al. | |
| 7,354,317 B2 | 4/2008 | Witham et al. | |
| 2002/0104972 A1 | 8/2002 | Guzorek | 250/504 |
| 2003/0011308 A1* | 1/2003 | Crawford et al. | 313/623 |
| 2004/0130255 A1* | 7/2004 | Mudra et al. | 313/318.08 |

FOREIGN PATENT DOCUMENTS

| | | |
|---|---|---|
| WO | WO 01/03099 A3 * | 5/2001 |
| WO | 2006136026 | 12/2006 |

OTHER PUBLICATIONS

Witham, et al. "Apparatus and Method for Keying lamp and Lamp Fixture," U.S. Appl. No. 60/440,908, filed Jan. 15, 2003. Specification having 11 pages, Figures having 3 sheets.

International Search Report, Application No. PCT/US07/20661, Date Mailed Jul. 28, 2008.

* cited by examiner

ULTRAVIOLET GERMICIDAL LAMP BASE AND SOCKET

FIELD OF THE INVENTION

The present invention relates in general to a lamp base and socket and more specifically to a lamp base and socket for inserting an ultraviolet lamp into an air or fluid duct for germicidal purposes.

BACKGROUND OF THE INVENTION

Many germicidal applications use ultraviolet gas discharge lamps. Ultraviolet gas discharge lamps are often placed in containers or ducts that contain a fluid, such as air or water. The ultraviolet radiation emitted from the ultraviolet gas discharge lamp has a germicidal effect destroying germs, viruses, and bacteria disinfecting the fluid. Often the ultraviolet gas discharge lamp is placed directly within the air flow in a conduit. In applications involving the disinfecting of a liquid, often a protective glass sleeve is used to surround the ultraviolet gas discharge lamp.

The ultraviolet gas discharge lamp should be easily installed, and installed so as to prevent ultraviolet radiation from escaping from the conduit or container. Often, as a safety feature, switches are used to prevent removal of the ultraviolet gas discharge lamp while the lamp is on so as to prevent exposure to potentially dangerous ultraviolet radiation. An ultraviolet lamp having a construction to prevent radiation when the lamp is removed from a duct is disclosed in U.S. Pat. No. 6,838,057 entitled "Power Disruption Apparatus for A radiation Lamp", and issuing to Russell et al on Jan. 4, 2005. Therein disclosed is a radiation lamp having a flange attached to the lamp base. An electrical socket is detachable mounted in a manner that prevents removal of the radiation lamp from duct without prior detachment of electrical socket from electrical pins.

Another ultraviolet lamp that can be quickly installed is disclosed in U.S. Pat. No. 6,797,966 entitled "Quick-install Irradiation Unit and Method of Making Same", and issuing to Summers et al on Sep. 28, 2004. Therein disclosed is an irradiation unit for irradiating a surface including a frame. The unit may be quickly installed in any orientation.

Another sterilization device is disclosed in U.S. Pat. No. 5,902,552 entitled "Ultraviolet Air Sterilization Device", and issuing to Brickley on May 11, 1999. Therein disclosed is an ultraviolet air sterilization device including a housing and mounts. A receptacle connects to corresponding mounts by means of a threaded connection enabling the lamp units to be easily removed.

While these prior devices have aided in the quick installation and safe operation of an ultraviolet germicide gas discharge lamp used to disinfect fluids, they often required relatively complicated mounting hardware and additional switches to prevent operation of the lamp upon removal from the fluid flowing in a duct or conduit. Therefore, there is a need for a more easily installed and safer operating ultraviolet germicidal gas discharge lamp for placement into a duct or container.

SUMMARY OF THE INVENTION

The present invention comprises a socket having a flange for mounting onto a fluid or air duct. The socket has a plurality of holes for providing electrical contact to an ultraviolet lamp. A base cap placed on the end of the ultraviolet lamp has a plurality of pins positioned adjacent a side of the base cap and pointed away from the end of the ultraviolet lamp and toward the opposing end of the ultraviolet lamp. Contact pin holes formed in the socket attached to the mounting flange attached to the fluid or air duct are adapted to receive the plurality of contact pins. A shield may be used to protect the plurality of pins from contact. A window may be placed in the end of the base cap to visually indicate that the ultraviolet lamp is energized and radiating. Additionally, the ultraviolet lamp and socket may be keyed to permit only a predetermined lamp in a predetermined angular orientation to mate and be connected.

It is an object of the present invention to provide an ultraviolet lamp that can easily be mounted in a fluid or air duct.

It is an object of the present invention to provide an ultraviolet lamp that is automatically de-energized upon removal from the fluid or air duct without the need for any separate switches.

It is an advantage of the present invention that the ultraviolet lamp is pushed directly into a socket engaging the contact pins.

It is an advantage of the present invention that upon removing the ultraviolet lamp from the fluid duct and socket the contact pins are disengaged, automatically removing power from the ultraviolet lamp, preventing the possibility of the ultraviolet lamp remaining on while unshielded by the duct.

It is another advantage of the present invention that direct visual confirmation of operation of the lamp can be made even when the lamp is completely enclosed in a duct.

It is a feature of the present invention that a contact pin shield extends from the base cap protecting the contact pins from inadvertent electrical contact or damage to the pins.

It is a feature of the present invention that the contact pins are placed adjacent the sides of the lamp and a distal end extends toward an opposing end of the lamp.

It is another feature of the present invention that a window is placed in the base cap.

These and other objects, advantages, and features will become more readily apparent in view of the following more detailed description.

DETAILED DESCRIPTION OF THE PREFERRED EMBODIMENT

Figure 1:
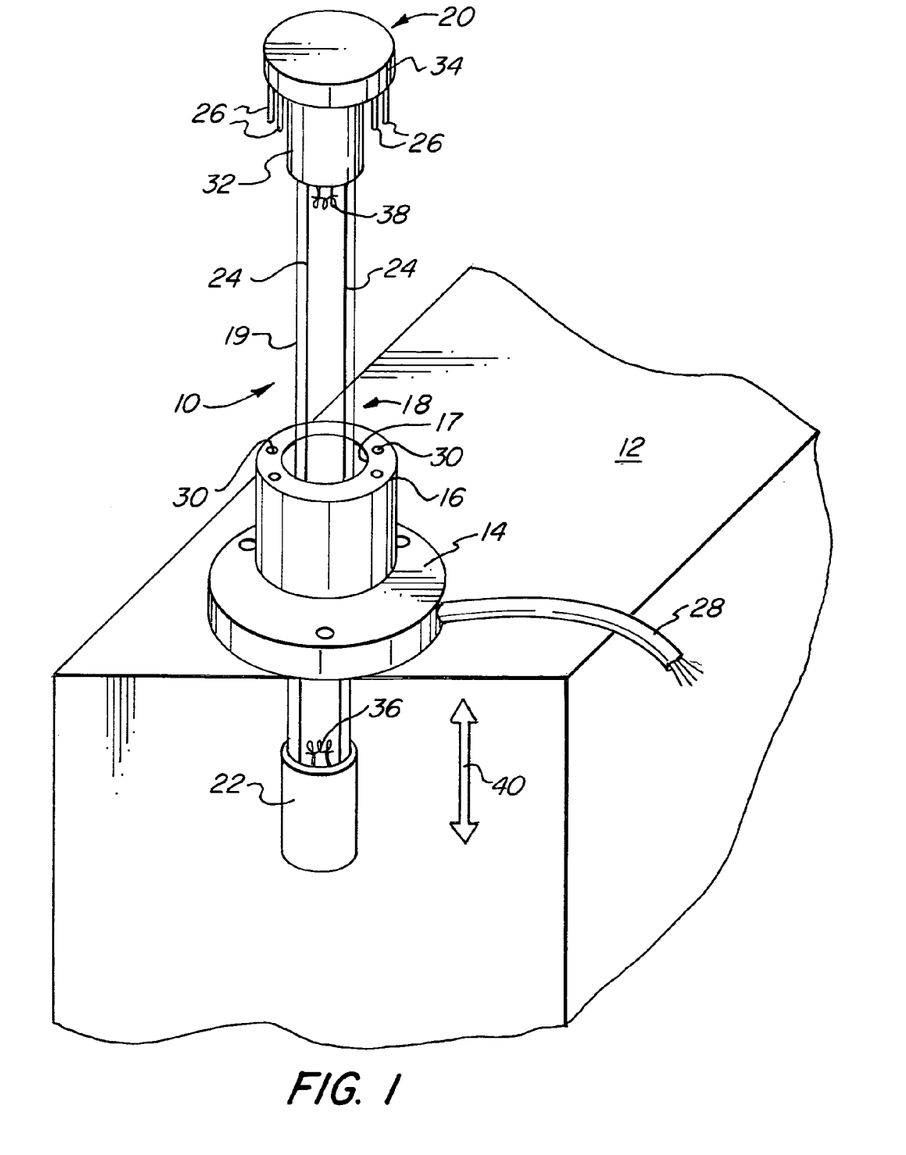
FIG. 1 schematically illustrates the placement of an embodiment of an ultraviolet lamp of the present invention in a fluid or air duct.

FIG. 1 illustrates an ultraviolet lamp fluid duct germicidal system 10. A fluid duct 12 has an opening therein on which a mounting flange 14 is placed. The fluid duct 12 may contain air or other gas or liquid such as water to be disinfected. The mounting flange 14 has a socket 16. The socket 16 has a plurality of contact pin holes 30 therein. A hole 17 is placed through the socket 16 and flange 14 and opens into the fluid duct 12. A lamp 18 is placed within the socket 16 and extends into the interior of the fluid duct 12. The lamp 18 is preferably an ultraviolet gas discharge or fluorescent lamp such as is commonly used in germicidal applications.

The lamp 18 has a base cap 20 on one end and an end cap 22 on the other. The base cap 20 comprises a disk cap 34 and a cylindrical base 32. The disk cap 34 extends radially sufficiently beyond the exterior surface of the lamp 18 so as to permit contact pins 26 to have the distal ends thereof extending downward towards the opposite end of the lamp 18 and away from the disk cap 34. A wire 24 provides an electrical connection between the base cap electrode 36 adjacent the base cap 22 and the contact pins 26 on the disk cap 34 on the base cap 20. One pair of the contact pins 26 are electrically connected to the base cap electrode 38. The other pair of contact pins 26 is coupled to the end cap electrode 36 through wires 24. Depending upon the number of contact pins used, one or more wire 24 may be used to provide an electrical connection to contact pins on a single end of the lamp 18. Power cable 28 is electrically connected to the socket 16 and provides power to the lamp 18. Arrow 40 represents the movement of the lamp 24 in and out of the fluid duct 12. The lamp 18 may preferably be an ultraviolet gas discharge lamp or an ultraviolet fluorescent lamp, but may by any other type of lamp having pin contacts, pin-like contacts, or other electrical contact.

Figure 2:
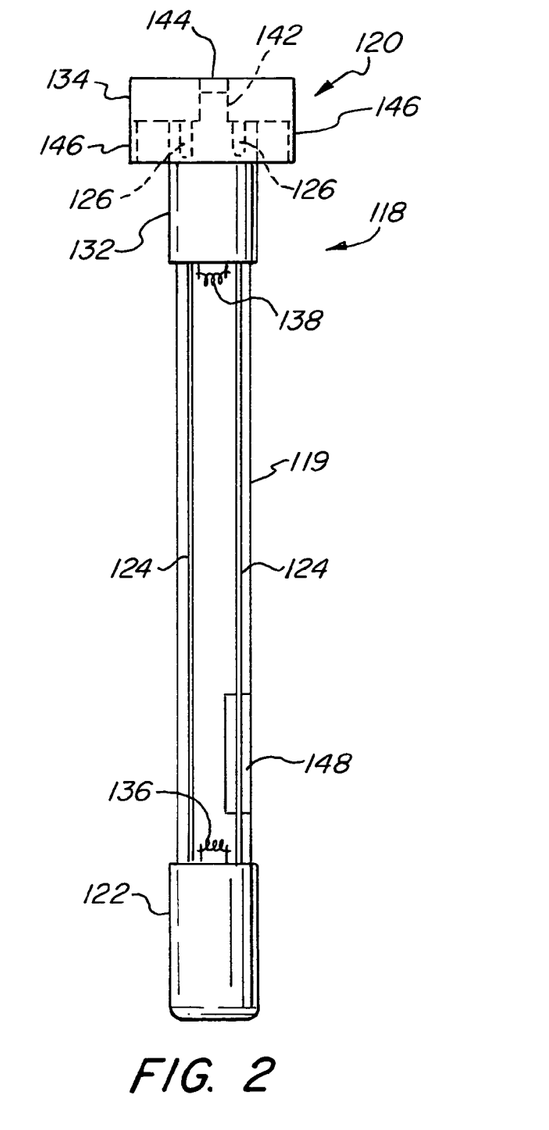
FIG. 2 is an elevational view of another embodiment of an ultraviolet lamp of the present invention.
Figure 3:
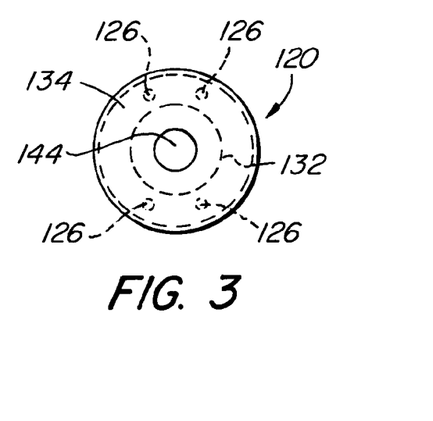
FIG. 3 is a top view of a base cap of the embodiment of the ultraviolet lamp illustrated in FIG. 2.

FIGS. 2 and 3 illustrates another embodiment of the present invention. In this embodiment a shield or guard 146 is used to protect the contact pins 126. The ultraviolet lamp 118 comprises a glass envelope 119 having a base cap 120 and an end cap 122. Electrodes 138 and 136 are placed adjacent each cap 120 and 122. Wires 124 electrically couple the electrode 136 to a pair of contact pins 126. The contact pins 126 are formed within the base cap 120. The base cap 120 comprises a cylindrical base attached to one end of the glass envelope 119. A disk cap 134 is formed on the cylindrical base cap 132 and has a diameter sufficiently greater than that of the glass envelope 119 and the cylindrical base cap 132 to permit contact pins 126 to be positioned along a side of the cylindrical base cap 132. The distal end of the contact pins 126 extend downward from the disk cap 134 towards the end cap 122 at the opposing end of the lamp 118. A pin shield 146 is formed on the edge of the disk cap 134 to protect a user or installer from inadvertently touching the contact pins 116 and also to protect the contact pins 126 from damage. The pin shield 146 guards the contact pins 126 from inadvertent contact and from being bent or damaged. Indicia 148 may be placed or etched on the glass envelope 119 to provide identifying information.

In this embodiment illustrated in FIGS. 2 and 3, a hole 142 is also formed in the disk cap 134 and extends through to the interior of the lamp 118. A transparent window 144 seals the external end of the hole 140. The transparent window 144 permits a view into the interior of the lamp 118. The window 144 permits visual confirmation that the lamp 118 is on when the lamp 118 is placed with a duct or conduit and only the end of the base cap 120 is visible.

FIG. 3 is a plan view of the base cap 120 more clearly illustrating the window 144 and contact pins 126. The four contact pins 126 are positioned around the disk cap 134 and extend downward adjacent the cylindrical base cap 132.

Figure 4:
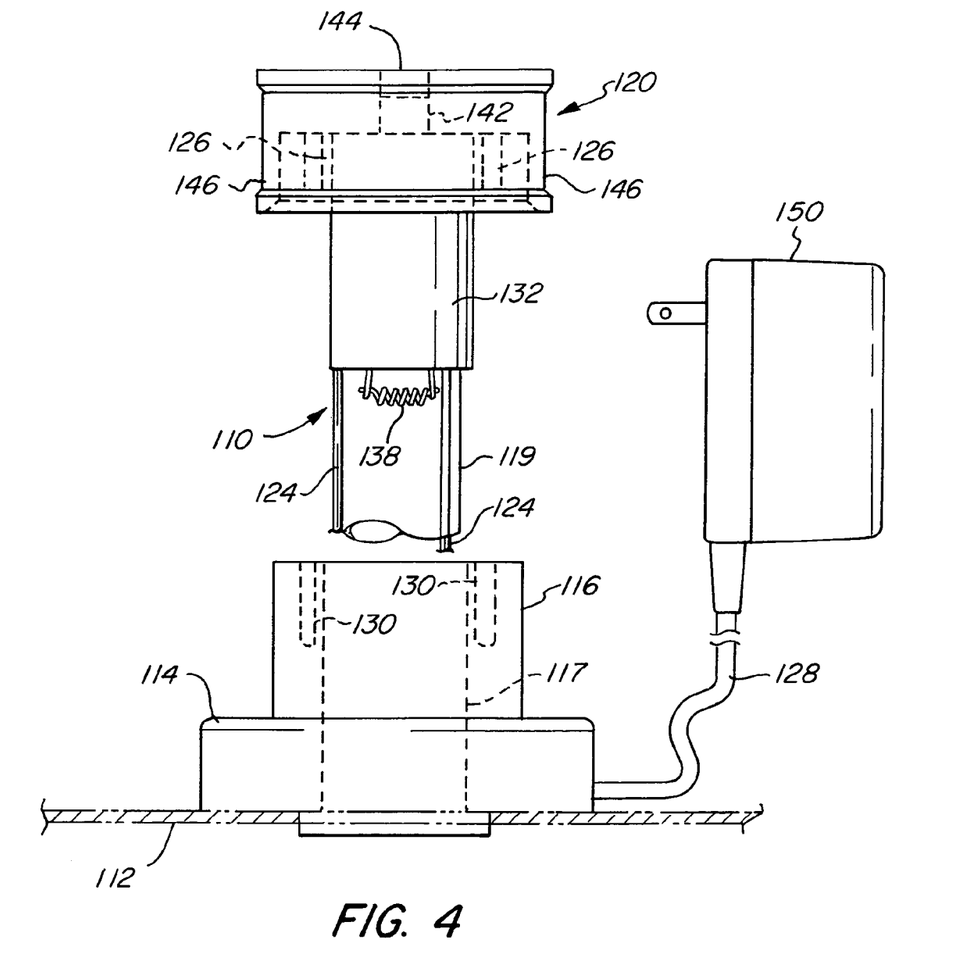
FIG. 4 is a partial elevational view of the embodiment of the ultraviolet lamp illustrated in FIGS. 2 and 3 being inserted into a socket.

FIG. 4 is an enlarged view of a portion of the germicidal ultraviolet lamp system 110, illustrating the base cap 120 and the socket 116 attached to a fluid chamber or duct 112. The mounting flange 114 may be mounted by any conventional means, such as screws, to a fluid chamber or duct 112. The socket 116 has a hole or bore 117 through which is placed the glass envelope 119 of the germicidal ultraviolet lamp. Contact pin holes 130 are formed within the socket 116 and are positioned and adapted to receive the contact pins 126 formed on the base cap 120. Contact pin shield 146 protects the contact pins 126. A power cord 128 is connected to a ballast or power supply 150 for powering the germicidal ultraviolet lamp. The contact pins 126 may be asymmetrically spaced on the base cap 120 to require a predetermined angular orientation of the lamp to connect or mate with the corresponding contact pin holes 130 in the socket 116.

Figure 5:
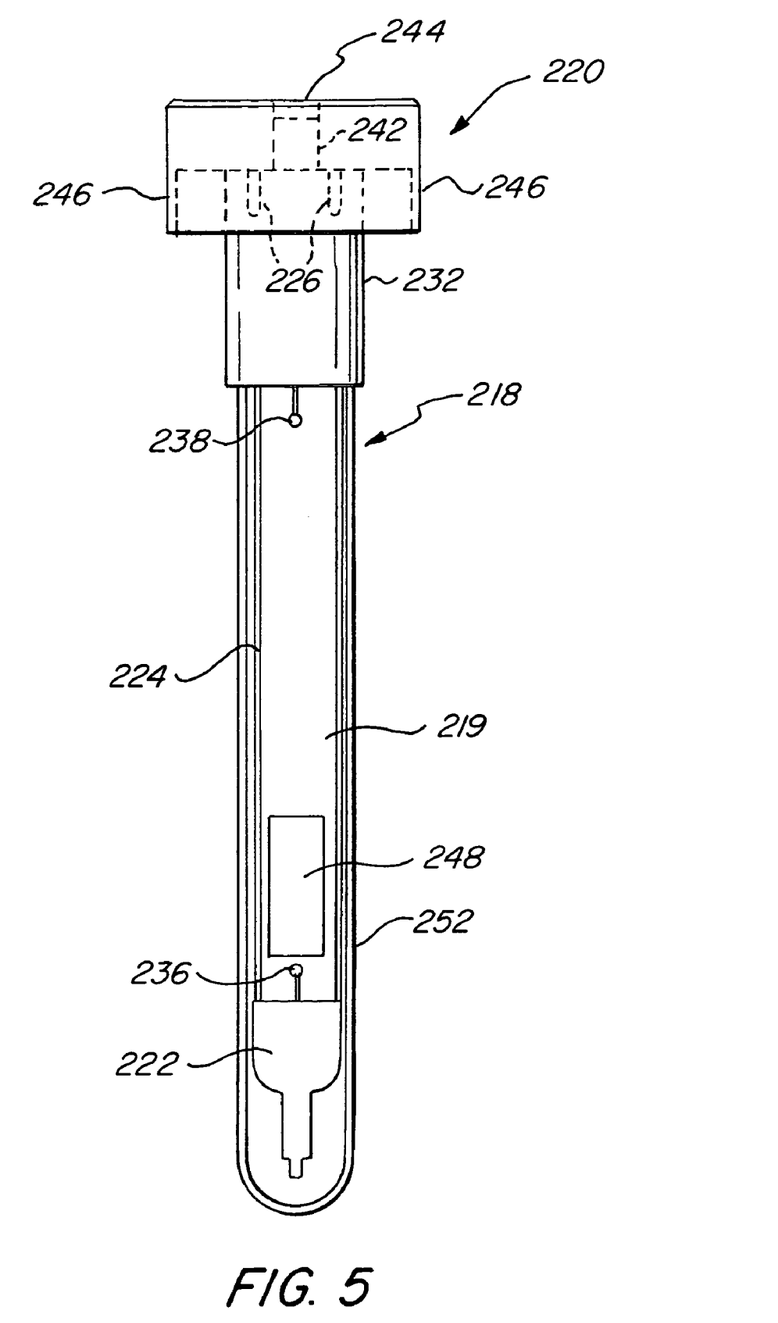
FIG. 5 is an elevational view of another embodiment of an ultraviolet lamp of the present invention having a protective tube.

FIG. 5 illustrates another embodiment of the present invention. In this embodiment a protective tube 252 is place over the glass envelope 219. The protective tube 252 is used to further protect the glass envelope 219, in air or especially when the fluid being treated is water or other liquid. In this embodiment, the lamp system 218 comprises a glass envelope 219 and end cap 222 positioned adjacent an electrode 236 at one end. Indicia 248 may be placed or etched onto the glass envelope 119 to identify the lamp system 218. Wires 224 electrically couple the end cap electrode 236 to one pair of the four contact pins 226. The cylindrical base 232 is attached to the protective tube 252 forming a seal and preventing fluids from contacting the glass envelope 219. The base cap 220 also has a hole 242 and window 244 formed therein, as well as a pin shield 246. The base cap electrode 238 is placed adjacent the cylindrical base 232 of the base cap 220. In this embodiment, illustrated in FIG. 5, the germicidal ultraviolet lamp system 218 may be installed as a unit into a chamber or duct containing fluid or air to be disinfected.

Figure 6:
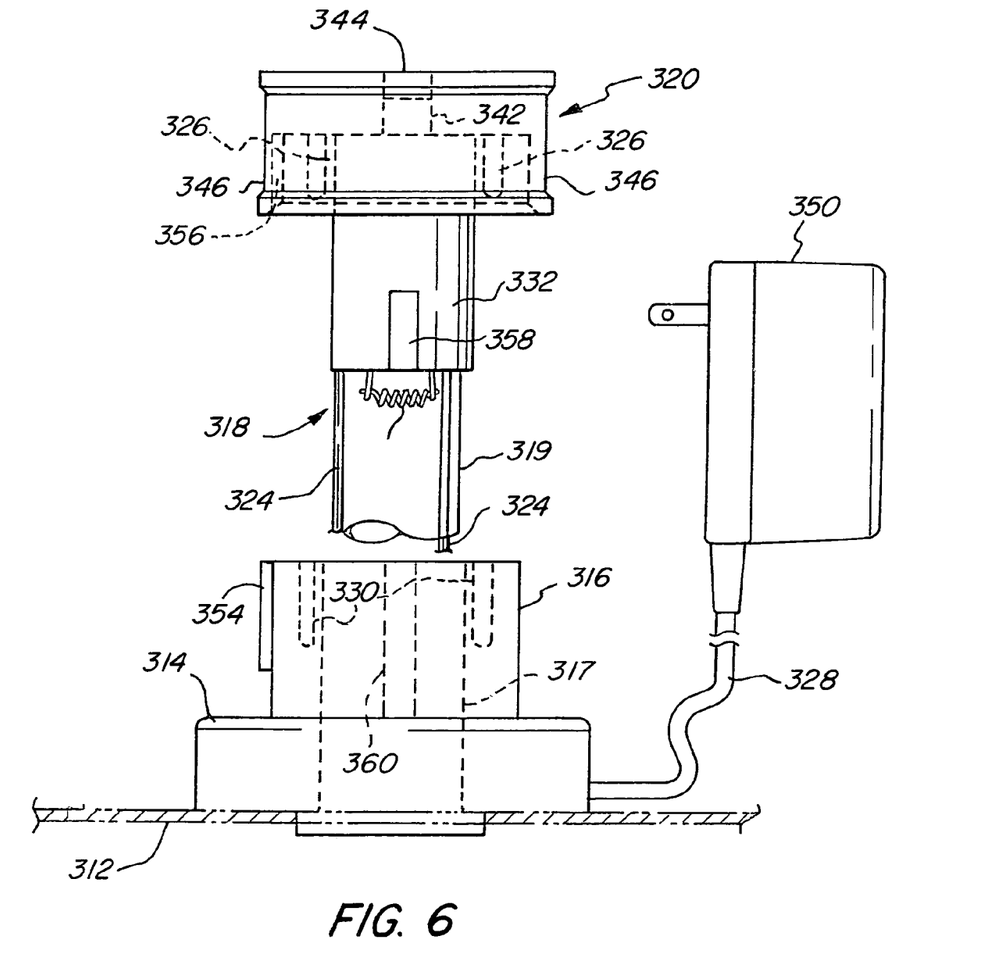
FIG. 6 is an elevational view of yet another embodiment of an ultraviolet lamp of the present invention having a lamp and socket mating system and electric line cord and power supply.

FIG. 6 illustrates another embodiment of the present invention. In this embodiment a key and receiver system is used to assure that the appropriate lamp is matched with the appropriate socket or application. That is, a specific power or type of lamp may have a key and mating receiver system that will only permit the correct lamp to fit a receiver on a socket. The key and receiver system may also be used to assure that the lamp is placed in a predetermined angular orientation within the chamber or duct, if desired.

In FIG. 6 a mounting flange 312 is attached to socket 316 having a hole 317 there through. Contact pin holes 330 are formed within socket 316. The contact pin holes 330 are coupled to a ballast or power supply 350 by power cord 328. The glass envelope 319 is adapted to be placed through a hole 317 within socket 316. The base cap 320 comprises a cylindrical base cap 332 attached to the glass envelope 319. Formed within the base cap 320 are contact pins 326. The contact pins 326 are protected by shield 346. A hole or opening 342 and window 344 is formed in the base cap 320.

A socket key 354 may be formed on socket 316 and a mating base receiver 356 may be formed within the pin shield 246. The socket key 354 and mating base receiver 256 may be used to assure that an appropriate lamp is used with the appropriate socket. The key and receiver may be reversed, as also illustrated in FIG. 6, with the base key 358 formed on the cylindrical base 332 and the mating socket receiver 360 formed on the socket 316. The key and receiver may be matched to prevent an inappropriate lamp from being energized causing potential injury or damage. While several different keys and receivers have been illustrated, other known methods may be used to physically match the lamp and the socket.

The present invention permits safe operation of an ultraviolet germicidal lamp for disinfecting a fluid flowing in a conduit or duct. The reverse or transposed contact pin arrangement of the present invention permits the ultraviolet germicidal lamp to be pushed or inserted into a socket on the conduit or duct directly without the need for any separate fixture attached to the base cap end.

While the ultraviolet germicidal lamp has been illustrated mounted in a vertical position or orientation, the ultraviolet germicidal lamp may also be mounted in a horizontal position or orientation, or at any angle. Additionally, upon removing the ultraviolet germicidal lamp from the conduit or duct the contact pins are automatically disengaged from the powered socket eliminating the need for a separate safety switch. This greatly improves safety by making it impossible to remove the ultraviolet germicidal lamp in an energized or radiating state eliminating the possibility of unintended exposure of dangerous ultraviolet radiation. Accordingly, the present invention greatly advances the art of disinfecting fluids with ultraviolet radiation.

While the present invention has been described with respect to several different embodiments, it will be obvious that various modifications may be made without departing from the spirit and scope of this invention.

What is claimed is:

1. A gas discharge lamp comprising:
a tubular glass envelope having a first end and a second end;
a base cap placed on the first end of said tubular glass envelope;
a disk cap connected to the base cap at an end of the base cap opposite from the second end of the tubular glass envelope, the disk cap having a radius larger than a radius of the base cap;
a contact pin formed on the disk cap and extending longitudinally toward the opposing second end of said tubular glass envelope; and
a pin shield extending from an outer edge of the disk cap in a direction toward the second end of said tubular glass envelope.

2. A gas discharge lamp as in claim 1 further comprising:
a window placed in said base cap,
whereby said window permits light to be seen when the lamp is operating providing visual confirmation that the gas discharge lamp is on.

3. A gas discharge lamp as in claim 1 further comprising:
an end cap placed on the second end of said tubular glass envelope; and
electrode wires extending along said tubular glass envelope coupling an electrode adjacent said end cap to said contact pin.

4. A gas discharge lamp as in claim 1 further comprising:
a key placed on said base cap; and
a receiver adapted to receive said key placed on a socket adapted to receive the gas discharge lamp,
whereby said key and receiver mate in a predetermined angular orientation.

5. An ultraviolet lamp used for disinfecting a fluid comprising:
a glass envelope having a first end and a second end;
a cylindrical base attached to the first end of said glass envelope;
a disk cap attached to said cylindrical base, said disk cap having a diameter greater than said cylindrical base;
contact pins extending from said disk cap along said cylindrical base and extending toward the second end of said glass envelope; and
a pin shield extending from an outer edge of the disk cap in a direction toward the second end of said glass envelope;
whereby the ultraviolet lamp is structured to be inserted within a chamber and said contact pins are structured to engage a socket.

6. An ultraviolet lamp used for disinfecting a fluid as in claim 5 further comprising:
a key placed on said disk cap.

7. An ultraviolet lamp used for disinfecting a fluid as in claim 6 further comprising:
a receiver adapted to receive said key placed on a socket adapted to receive the ultraviolet lamp,
whereby said key and receiver mate in a predetermined angular orientation.

8. An ultraviolet lamp used for disinfecting a fluid as in claim 6 further comprising:
a protective tube placed over said glass envelope.

9. An ultraviolet lamp used for disinfecting a fluid comprising:
a tubular glass envelope having a first end and a second end;
a cylindrical base attached to the first end of said tubular glass envelope;
a disk cap attached to said cylindrical base, said disk cap having a diameter greater than said cylindrical base;
contact pins extending from said disk cap along said cylindrical base and having distal ends extending from said disk cap and toward the second end of said tubular glass envelope; and
a pin shield extending from an outer edge of the disk cap in a direction toward the second end of said glass envelope,
whereby the ultraviolet lamp is structured to be inserted within a chamber, said contact pins are structured to engage a socket, and said contact pins are protected from inadvertent contact and damage by said cylindrical shield.

10. An ultraviolet lamp used for disinfecting a fluid as in claim 9 further comprising:
a window placed in said disk cap,
whereby said window permits light to be seen when the lamp is operating providing visual confirmation that the ultraviolet lamp is on.

11. An ultraviolet lamp used for disinfecting a fluid as in claim 9 further comprising:
a key placed on said disk cap.

12. An ultraviolet gas discharge lamp assembly comprising:
a glass envelope having a first end and a second end;
a protective tube covering said glass envelope;
a cylindrical base attached to the first end of said glass envelope;
a disk cap attached to said cylindrical base, said disk cap having a diameter greater than said cylindrical base;
contact pins extending from said disk cap along said cylindrical base and extending toward the second end of said glass envelope; and
a pin shield extending from an outer edge of the disk cap in a direction toward the second end of said glass envelope;
whereby the ultraviolet lamp is structured to be inserted within a chamber, and said contact pins are structured to engage a socket.

13. An ultraviolet gas discharge lamp assembly as in claim 12 further comprising:
a window placed in said disk cap,
whereby said window permits light to be seen when the ultraviolet gas discharge lamp is operating providing visual confirmation that the ultraviolet gas discharge lamp is on.

14. An ultraviolet gas discharge lamp assembly as in claim 12 further comprising:
a key placed on said cylindrical base or disk cap; and
a receiver adapted to receive said key placed on a socket adapted to receive the ultraviolet gas discharge lamp, whereby said key and receiver mate in a predetermined angular orientation.

15. An ultraviolet lamp used for disinfecting a fluid comprising:
- a glass envelope having a first end and a second end;
- a cylindrical base attached to the first end of said glass envelope;
- a disk cap attached to said cylindrical base, said disk cap having a diameter greater than said cylindrical base;
- contact pins extending from said disk cap along said cylindrical base and extending toward the second end of said glass envelope;
- a shield attached to said disk cap and extending from said disk cap toward the second end of said glass envelope; and
- means for mating with a socket, formed on said cylindrical base, disk cap, or shield,
- whereby the ultraviolet lamp structured to be inserted within a chamber and said contact pins are structured to engage the socket.

16. An ultraviolet lamp used for disinfecting a fluid as in claim 15 wherein:
- said means for mating with a socket comprises a key.

17. An ultraviolet lamp used for disinfecting a fluid as in claim 15 wherein:
- said means for mating with a socket comprises a receiver.

18. An ultraviolet lamp used for disinfecting a fluid as in claim 15 further comprising:
- a window formed in said disk cap,
- whereby said window permits light to be seen when the ultraviolet lamp is operating providing visual confirmation that the ultraviolet lamp is on.

19. An ultraviolet lamp and socket system used for disinfecting a fluid in a chamber suitable for holding the fluid comprising:
- a glass envelope having a first end and a second end;
- a cylindrical base attached to the first end of said glass envelope;
- a disk cap attached to said cylindrical base, said disk cap having a diameter greater than said cylindrical base;
- contact pins extending from said disk cap along said cylindrical base and extending toward the second end of said glass envelope;
- a pin shield extending from an outer edge of the disk cap in a direction toward the second end of said glass envelope
- a socket structured to attach to the chamber, said socket having a hole there through adapted to receive said glass envelope and said cylindrical base, said socket having contact pin holes positioned to receive said contact pins, wherein said contact pins enter the contact pin holes upon advancing said glass envelope and said cylindrical base through the holes in said socket;
- whereby the ultraviolet lamp is structured to be inserted within the chamber and powered only when said contact pins are caused to engage the contact pin holes in said socket, and the ultraviolet lamp is fully enclosed by the chamber thereby preventing any inadvertent exposure outside of the chamber to ultraviolet radiation from the energized ultraviolet lamp.

20. An ultraviolet lamp and socket system used for disinfecting a fluid as in claim 19 further comprising:
- a window placed in said disk cap,
- whereby said window permits light to be seen when the ultraviolet lamp is operating providing visual confirmation that the ultraviolet lamp is on.

21. A base cap to be fitted on an end of a glass envelope and designed to couple with a socket, the base cap comprising:
- a cylindrical base comprising a first end and a second end, the first end being open to receive the glass envelope therein;
- a disk cap connected to the second end of the cylindrical base, the disk cap having a radius larger than a radius of the cylindrical base;
- at least one contact pin formed on the disk cap and extending toward the first end of the cylindrical base; and
- a pin shield connected to an outer edge of the disk cap and extending toward the first end of the cylindrical base.

* * * * *